United States Patent
Yamamoto et al.

(10) Patent No.: US 7,282,354 B2
(45) Date of Patent: *Oct. 16, 2007

(54) METHOD FOR PRODUCING FERMENTED MILK PRODUCT

(75) Inventors: Naoyuki Yamamoto, Sagamihara (JP); Natsue Kawakami, Yokohama (JP); Yuu Ishida, Tokyo (JP); Hirokazu Yada, Kawasaki (JP)

(73) Assignee: Calpis Co., Ltd., Tokyo (JP)

( * ) Notice: Subject to any disclaimer, the term of this patent is extended or adjusted under 35 U.S.C. 154(b) by 455 days.

This patent is subject to a terminal disclaimer.

(21) Appl. No.: 10/310,628

(22) Filed: Dec. 5, 2002

(65) Prior Publication Data

US 2003/0064501 A1    Apr. 3, 2003

Related U.S. Application Data

(62) Division of application No. 09/508,840, filed on Mar. 16, 2000, now Pat. No. 6,534,304.

(51) Int. Cl.
*A23C 9/12* (2006.01)
*A23C 9/123* (2006.01)
*C12N 1/20* (2006.01)

(52) U.S. Cl. .............. 435/71.2; 435/252.9; 435/68.1; 426/61; 426/63; 424/93.45

(58) Field of Classification Search ............ 435/252.9, 435/68.1, 71.1, 71.2; 424/93.45; 426/61, 426/63

See application file for complete search history.

(56) References Cited

U.S. PATENT DOCUMENTS

| | | | |
|---|---|---|---|
| 3,846,560 A | 11/1974 | Hempenius et al. | |
| 3,876,806 A | 4/1975 | Hempenius et al. | |
| 4,107,334 A | 8/1978 | Jolly | |
| 4,293,571 A | 10/1981 | Olofsson et al. | |
| 4,585,757 A | 4/1986 | Pang et al. | 514/18 |
| 4,687,739 A | 8/1987 | Sugisawa et al. | |
| 4,687,840 A | 8/1987 | Pang et al. | 530/331 |
| 5,238,921 A | 8/1993 | Maruyama et al. | 514/18 |
| 5,314,873 A | 5/1994 | Tomita et al. | 514/21 |
| 5,409,718 A | 4/1995 | Klaver et al. | 426/42 |
| 5,418,218 A | 5/1995 | Wilber | 514/11 |
| 5,466,472 A | 11/1995 | Kuma et al. | 426/43 |
| 5,486,461 A | 1/1996 | Nielsen | 435/68.1 |
| 5,547,687 A | 8/1996 | Outinen et al. | |
| 5,618,689 A | 4/1997 | McCarthy et al. | |
| 5,656,268 A | 8/1997 | Sorodsky | 424/93.45 |
| 6,214,585 B1 | 4/2001 | Kwon et al. | 435/71.2 |
| 6,221,423 B1 | 4/2001 | Cho et al. | 426/656 |
| 6,372,282 B1 | 4/2002 | Edens et al. | 426/656 |
| 2002/0132288 A1 | 9/2002 | Swamylingappa et al. | 435/68.1 |
| 2002/0182301 A1 | 12/2002 | Draaisma et al. | 426/583 |
| 2003/0027769 A1 | 2/2003 | Scialdone et al. | 514/18 |
| 2003/0040475 A1 | 2/2003 | Toba et al. | 514/12 |
| 2003/0072863 A1 | 4/2003 | Hayasawa et al. | 426/580 |

FOREIGN PATENT DOCUMENTS

| | | | |
|---|---|---|---|
| JP | 06-197786 | * | 7/1994 |
| WO | WO 01/68113 A1 | | 9/2001 |
| WO | WO 01/68114 A1 | | 9/2001 |

OTHER PUBLICATIONS

Nakamura et al., Dairy Sci., 78:777-783 1995.*
Biosciences and Industry, Susumu Maruyama, "Production of Hypotensive Peptides from Food Protein", 47 No. 11, 38-42, 1989. (with partial translation).
Japan Fermentation Engineering Society, Susumu Maruyama, et al. "Production of Peptide Inhibitors of the Renin-Angiotensin System from Maize Protein", p. 23, 1988.
Japanese Society for Bioscience, Biotechnology and Agrochemistry, Susumu Maruyama, et al., "Angiotensin Converting Enzyme Inhibitory Effect and Hypotensive Effect of Peptides from Repeat Sequence Region of Corn Seed Protein", p. 8, 1989.
Japan Nutrition and Food Society, Shinsuke Miyoshi, et al., "Hypotensive Effect of Enzymolytic Product of Maize Protein on SHR", p. 113, 1989.
Journal of Japan Agricultural Chemistry Society, Shinsuke Miyoshi, et al., "Angiotensin Converting Enzyme Inhibitory Effect of Peptides Derived from Maize Protein", 64(3), 555, 1990. (translation).
Antonie van Leeuwenhoek, "The Proteolytic Systems of Lactic Acid Bacteria," 70: 187-221. 1996.

* cited by examiner

*Primary Examiner*—Irene Marx
(74) *Attorney, Agent, or Firm*—Darby & Darby

(57) ABSTRACT

There is provided a fermented milk product that contains lactic acid bacteria capable of producing a large amount of lactotripeptide and a large amount of active ingredient having hypotensive activity and anti-stress effect, and that can be taken pleasantly as foods or beverages. Lactic acid bacteria of *Lactobacillus helveticus* having specific bacteriological properties, the bacteria, when cultured in a medium of animal milk containing 9 wt % solid of non-fat milk, producing tripeptides Val-Pro-Pro and Ile-Pro-Pro in an amount of 60 μg in terms of Val-Pro-Pro per ml medium, and the bacteria exhibiting extracellular proteinase activity of not lower than 400 U/OD$_{590}$. *Lactobacillus helveticus* CM4 strain (deposited at National Institute of Bioscience and Human-Technology Agency of Industrial Science and Technology, deposition number FERM BP-6060). A fermented milk product obtained by fermenting an animal milk with these lactic acid bacteria.

3 Claims, 1 Drawing Sheet

METHOD FOR PRODUCING FERMENTED MILK PRODUCT

This is a division of application Ser. No. 09/508,840, filed Mar. 16, 2000, now U.S. Pat. No. 6,534,304 which is hereby incorporated herein by reference, in its entirety.

FIELD OF ART

The present invention relates to novel lactic acid bacteria of *Lactobacillus helveticus* that can produce a particular tripeptide with high efficiency when they are cultured in an animal milk medium and that have high extracellular proteinase activity; a fermented milk product containing the lactic acid bacteria; and a method for producing the product.

BACKGROUND ART

*Lactobacillus helveticus* has been employed for producing fermented milk for a long time as a typical lactic acid bacteria starter for dairy milk products. *Lactobacillus helveticus* has high proteolytic activity, and particularly, its extracellular proteinase having high activity plays an important role in fermentation of animal milk. That is, the extracellular proteinase digests animal milk proteins to produce various peptide fragments. The produced peptides are further subjected to the action of peptidases to become peptides of lower molecular weight. It is known that a part of peptides produced in a medium due to the action of proteinase enzymes is taken into cells of the lactic acid bacteria and utilized as a nitrogen source. It has also been reported that some of the peptides produced in the medium have an inhibitory activity against angiotensin converting enzyme (ACE) which causes hypertension. (J. Dairy Sci. 78:777-783(1995)).

As peptides for inhibiting ACE activity and suppressing rise in blood pressure, various effective peptides have been reported, such as those derived from degradation products of milk proteins, soybean proteins or fish meat proteins. For example, Val-Pro-Pro and Ile-Pro-Pro (abbreviated hereinbelow as VPP and IPP, respectively. These peptides are collectively referred to hereinbelow as lactotripeptides) are known as peptides having ACE inhibitory activity present in a *Lactobacillus helveticus*—fermented milk. These lactotripeptides have been confirmed to have a strong hypotensive effect by experiments using spontaneously hypertensive rat (SHR) (J. Dairy Sci. 78:1253-1257(1995)).

However, the lactotripeptide-containing fermented milk produced by fermenting animal milk with conventional *Lactobacillus helveticus* strains can hardly be taken as it is, because it exhibits high acidity due to a large quantity of lactic acid generated as the fermentation progresses. Dilution of the fermented milk results in extreme decrease in the content of the lactotripeptides.

Thus, it is desired to produce fermented milk with higher content of the lactotripeptides compared to the content of the lactic acid generated in the fermented milk. With an addition of a small amount of such fermented milk to various foods and beverages, products having the function of the lactotripeptides could be prepared easily and provided to consumers in an agreeable form to take. However, none of known lactic acid bacteria strains produce the lactotripeptide with high efficiency.

DISCLOSURE OF THE INVENTION

It is an object of the present invention to provide a novel lactic acid bacteria strain which can produce a large amount of lactotripeptide with high efficiency with respect to the amount of the generated lactic acid.

It is another object of the present invention to provide a fermented milk product which contains the lactotripeptide having activities such as hypotensive activity and expected to have anti-stress effect, and a lactic acid bacteria strain capable of producing a large amount of this lactotripeptide and which can be taken pleasantly as foods or beverages, and a method for producing the same.

According to the present invention, there is provided lactic acid bacteria of *Lactobacillus helveticus* having the following bacteriological properties, said bacteria, when cultured in a medium of animal milk containing 9 wt % solid of non-fat milk, producing tripeptides Val-Pro-Pro and Ile-Pro-Pro in an amount of not less than 60 µg in terms of Val-Pro-Pro per ml medium, and said bacteria exhibiting extracellular proteinase activity of not lower than 400 $U/OD_{590}$:

(Morphological Properties)
1) Shape of Cell; rod,
2) Motility; none,
3) Spore Formation; none,
4) Gram Stain; positive (Physiological Properties)
1) Catalase Production; negative,
2) Indole Production; negative,
3) Nitrate Reduction; negative,
4) Aerobic Growth; facultative anaerobic,
5) Formation of DL-lactic acid from glucose by homolactic fermentation without formation of gases
6) Carbohydrate Degradation
glucose; +
lactose; +
mannose; +
fructose; +
galactose; +
sucrose; −
maltose; −
xylose; −
rhamnose; −
cellobiose; −
trehalose; −
melibiose; −
raffinose; −
stachyose; −
mannitol; −
sorbitol; −
esculin; −
salicin; −.

According to the present invention, there is also provided the lactic acid bacteria of *Lactobacillus helveticus* wherein said lactic acid bacteria is *Lactobacillus helveticus* CM4 strain (deposited at National Institute of Bioscience and Human-Technology Agency of Industrial Science and Technology on Aug. 15, 1997, deposition number FERM BP-6060).

According to the present invention, there is further provided the lactic acid bacteria of *Lactobacillus helveticus* having a chromosomal DNA which gives a DNA fragment of 15 to 17 kb when said chromosomal DNA is digested with restriction enzymes PstI and EcoRI.

According to the present invention, there is also provided a fermented milk product containing a fermented milk comprising the aforementioned lactic acid bacteria, and a tripeptide selected from the group consisting of Val-Pro-Pro, Ile-Pro-Pro and mixtures thereof.

According to the present invention, there is also provided a method for producing a fermented milk product comprising fermenting a medium containing a food material selected from the group consisting of a peptide, a protein and mixtures thereof including sequence Val-Pro-Pro and Ile-Pro-Pro, with the lactic acid bacteria.

PREFERRED EMBODIMENTS OF THE INVENTION

Figure 1:
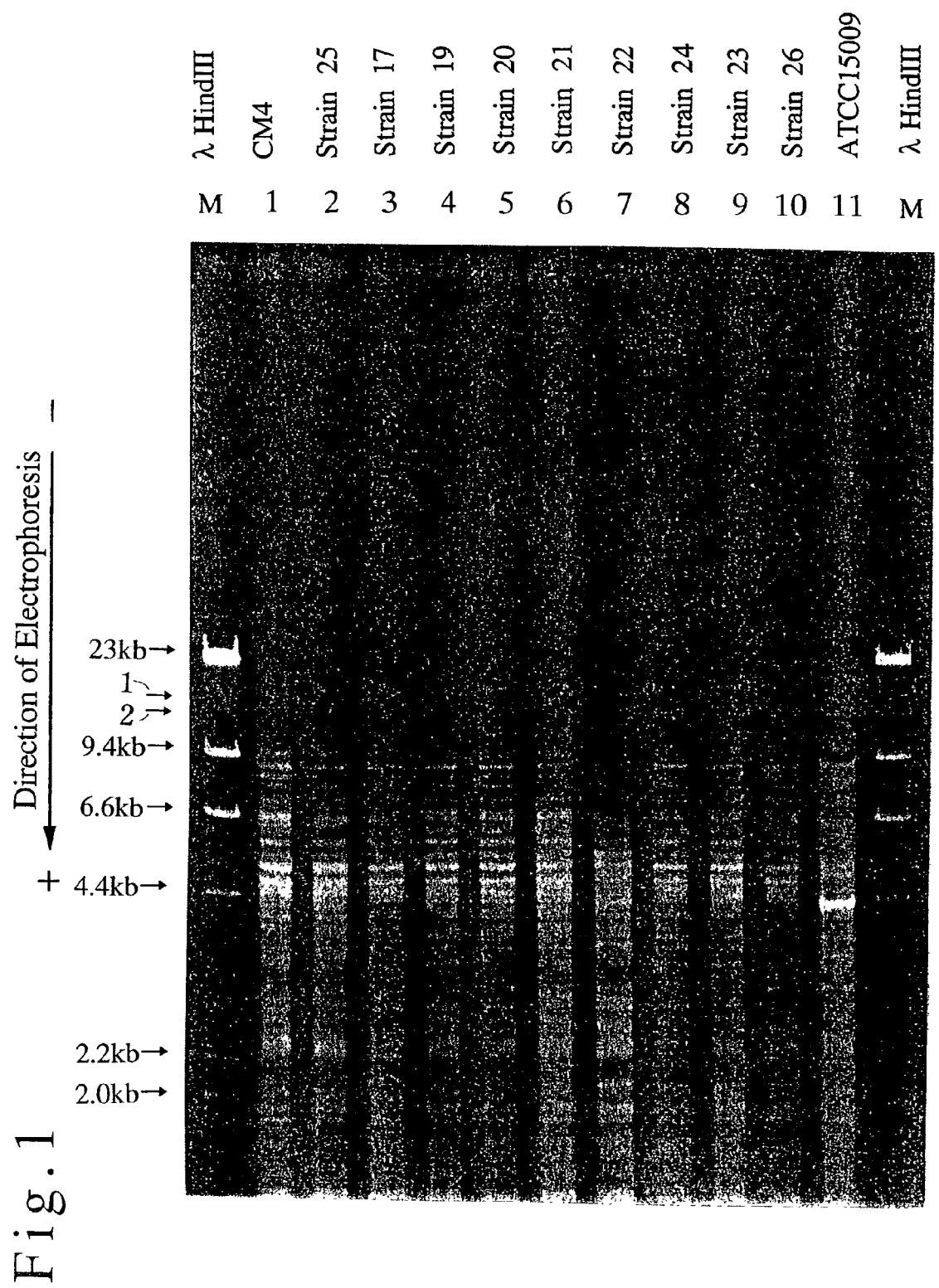
FIG. 1 is a photograph showing the agarose gel electrophoresis pattern of chromosomal DNA fragments of various *Lactobacillus helveticus* strains in Example 2.

The lactic acid bacteria of the present invention belong to *Lactobacillus helveticus*, and characterized in that the lactic acid bacteria produce tripeptides Val-Pro-Pro and Ile-Pro-Pro in an amount of not less than 60 μg, and preferably not less than 70 μg in terms of Val-Pro-Pro per ml medium when cultured in a medium of animal milk containing 9 wt % solid of non-fat milk, and exhibits extracellular proteinase activity of not lower than 400 $U/OD_{590}$, and preferably not lower than 430 $U/OD_{590}$. The defined lactotripeptide productivity is an index to distinguish the present lactic acid bacteria from conventional lactic acid bacteria of *Lactobacillus helveticus*. For example, by this index is defined a property of the present lactic acid bacteria to produce, when cultured in animal milk containing 9 wt % solid of non-fat milk, the lactotripeptides in an amount of not less than 60 μg in terms of VPP per ml medium, which could not have been realized with the conventional lactic acid bacteria. Usually, the lower the content of the solid of non-fat milk in the medium for culturing, the smaller the amount of the lactotripeptides to be produced. The higher the content of the solid of non-fat milk, the larger the amount of the lactotripeptide.

The productivity of the lactotripeptides as the index is measured by the steps of inoculating with the lactic acid bacteria animal milk, such as cow's milk, goat's milk, horse's milk, and skim milks thereof, containing 9 wt % solid of non-fat milk, culturing the bacteria at 37° C. for 24 hours to prepare fermented milk, centrifuging 1 ml of the fermented milk at 15,000 rpm for 10 minutes, subjecting the supernatant to measurement for the amounts of VPP and IPP, and converting the amounts into the VPP amount. Converted amount of the lactotripeptide in terms of VPP is calculated by the following equation since ACE inhibitory activity of IPP per unit weight is 1.7 times that of VPP:

Converted amount of lactotripeptide (μg in terms of *VPP* per ml)=amount of *IPP* (μg/ml)×1.7+ amount of *VPP* (μg/ml).

The maximum lactotripeptide productivity is not particularly limited, but can be achieved when all of Val-Pro-Pro and Ile-Pro-Pro included as the sequences in the protein of the medium are taken out as the tripeptides by digestion.

The extracellular proteinase activity is measured in accordance with the method of Yamamoto et al. (Yamamoto, N. et al. J. Biochem. (1993)114, 740) based on the method of Twining et al. (Twining, S. Anal. Biochem. 143 3410 (1984)), and expressed by defining the amount of enzyme exhibiting 1% fluorescent intensity to be 1 $U/OD_{590}$. The upper limit of the extracellular proteinase activity is not limited either, but is usually 800 $U/OD_{590}$.

The present lactic acid bacteria can produce a large amount of the lactotripeptide with respect to the amount of the lactic acid generated during fermentation. Thus, fermentation using the present lactic acid bacteria results in a fermented milk containing a larger amount of the lactotripeptide compared to a fermented milk containing the similar amount of lactic acid prepared with conventional lactic acid bacteria. The lactic acid due to such fermentation is DL-lactic acid. The amount of the lactotripeptide produced by fermentation with the present lactic acid bacteria is preferably not less than 30 μg in terms of VPP per 1 ml of the resulting fermented milk containing 0.01 g/ml of DL-lactic acid generated during the fermentation. The upper limit of the amount of the lactotripeptide is not particularly limited, but it is possible for the bacteria to produce up to about 50 μg in terms of VPP per 1 ml of the fermented milk containing 0.01 g of DL-lactic acid. The amount of DL-lactic acid is roughly proportional to the amount of the lactotripeptide. Therefore, for example, when 0.02 g of DL-lactic acid is produced in 1 ml of the fermented milk, the amount of the lactotripeptide production is preferably not less than 60 μg in terms of VPP. On the contrary, by the fermentation with the conventional lactic acid bacteria, the amount of the lactotripeptide is, at most, less than 30 μg in terms of VPP per 0.01 g of DL-lactic acid in 1 ml of fermented milk.

As an example of the present lactic acid bacteria, *Lactobacillus helveticus* CM4 strain is deposited as FERM BP-6060 at National Institute of Bioscience and Human-Technology Agency of Industrial Science and Technology (deposited on Aug. 15, 1997). *Lactobacillus helveticus* CM4 strain has the following bacteriological properties:

1. Morphological Properties
   1) Shape of Cell; rod,
   2) Motility; none,
   3) Spore Formation; none,
   4) Gram Stain; positive
2. Physiological Properties
   1) Catalase Production; negative,
   2) Indole Production; negative,
   3) Nitrate Reduction; negative,
   4) Aerobic Growth; facultative anaerobic,
   5) Formation of DL-lactic acid from glucose by homolactic fermentation without formation of gases
   6) Carbohydrate Degradation
      glucose; +
      lactose; +
      mannose; +
      fructose; +
      galactose; +
      sucrose; −
      maltose; −
      xylose; −
      rhamnose; −
      cellobiose; −
      trehalose; −
      melibiose; −
      raffinose; −
      stachyose; −
      mannitol; −
      sorbitol; −
      esculin; −
      salicin; −

The aforementioned bacteriological properties of CM4 strain are identical with publicly known *Lactobacillus helveticus* NCDO-099 strain when examined by the method of Mitsuoka et al. (Rinshoukensa 18, 1163(1974)). However, as to the following properties, which are not described in Mitsuoka et al., CM4 is clearly distinguished from NCDO-099.

7) Extracellular proteinase activity; not less than 400 $U/OD_{590}$

8) Lactotripeptide productivity; production of two sorts of tripeptides (VPP and IPP) in an amount of 60 µg or more in terms of VPP per ml fermented liquid when cultured in a medium containing 9 wt % skim milk at 37° C. for 24 hours.

The lactotripeptide productivity in 8) is measured using skim milk as solid of non-fat milk.

The lactic acid bacteria strain of the present invention may be obtained by the following screening and measurement of extracellular proteinase activity.

(1) Primary Screening (Selection of Strain by Measurement of High ACE Inhibitory Activity in the Fermented Milk)

The strains to be screened are cultured in a 9 wt % skim milk medium at 37° C. for 24 hours. After finishing the culturing, the number of the lactic acid bacteria, acidity of the lactic acid, and ACE inhibitory activity are measured. Strains producing $1 \times 10^8$ cells/ml or more of lactic acid bacteria, and exhibiting acidity of the lactic acid of 1.6 wt % or more and ACE inhibitory activity of 40 unit/ml or more are selected. ACE inhibitory activity is measured by Cushman and Cheung's method (Cushman, D. W. and Cheung, H. S. Pharmacol., 20 1637(1971)).

(2) Secondary Screening (Selection of Strain Having High Lactotripeptide Productivity)

The cultured liquids of the strains selected by the primary screening are centrifuged at 15,000 rpm for 10 minutes, and the supernatants thereof are subjected to HPLC for quantifying the lactotripeptide. Strains which produced not less than 50 µg in terms of VPP per ml are selected.

(3) Measurement of Extracellular Proteinase Activity

Each of the strains selected by the secondary screening is cultured in a 9 wt % skim milk medium while pH thereof is maintained at 6. Sample is taken in the middle of logarithmic growth phase, and admixed with 1 wt % of sodium citrate, and centrifuged at 5,000 rpm for 10 minutes to harvest cells. The harvested cells were washed with 50 mM β-glycerophosphoric acid, and suspended in 50 mM Tris-HCl buffer (pH 7.8) to adjust turbidity ($OD_{590}$) to 1. Proteinase activity on the cell surface is then measured. It will be confirmed that the result is correlative with lactotripeptide productivity of strains measured in the secondary screening.

The lactic acid bacteria strain of *Lactobacillus helveticus* selected by the above method can be identified and distinguished from other lactic acid bacteria strains by, e.g., the aforementioned lactotripeptide productivity and extracellular proteinase activity.

The lactic acid bacteria of the present invention preferably has, in addition to the aforementioned lactotripeptide productivity and extracellular proteinase activity, chromosomal DNA which gives a DNA fragment of 15 to 17 kb when the chromosomal DNA is digested with restriction enzymes PstI and EcoRI. Therefore, the lactic acid bacteria of the present invention can clearly be distinguished from other strains of the same species by examining whether the strain has the chromosomal DNA which gives such a DNA fragment.

The existence of the DNA fragment of 15 to 17 kb may be confirmed by extracting the chromosomal DNA of the lactic acid bacteria in accordance with the method of Leenhouts et al. (Leenhouts, K. (1990) Appl. Environ. Microbiol. 56:2726), digesting the chromosomal DNA with EcoRI and PstI, performing 0.8% agarose gel electrophoresis of the digested fragments, and analyzing the resulting electrophoresis pattern. Upon electrophoresis, the existence of the DNA fragment is clearly confirmed by subjecting λ phage DNA digested with a restriction enzyme Hind III to parallel electrophoresis as a size marker.

The fermented milk product of the present invention contains, as a requisite component, fermented milk containing the lactic acid bacteria and the tripeptide selected from the group consisting of VPP, IPP and mixtures thereof. That is, the fermented milk product of the present invention contains fermented milk containing the lactotripeptide and the lactic acid bacteria, and prepared by fermentation of a medium containing a food material composed of peptides and/or proteins including the sequence VPP and/or IPP with the lactic acid bacteria of the present invention. Thus, the contents of the lactic acid bacteria and the tripeptide may be suitably selected depending on the sort of the fermented milk product to be prepared. The present fermented milk product may contain the obtained fermented product itself, a diluted fermented product, or a purified fermented product.

The fermented milk product of the present invention contains DL-lactic acid generated during the fermentation. The fermented milk product of the present invention preferably contains the lactotripeptide in an amount of 30 to 50 µg in terms of VPP with respect to 0.01 g of the DL-lactic acid. The amount of the DL-lactic acid is roughly proportional to the amount of the lactotripeptide. Thus, if the fermented milk product contains a concentrated fermented milk and contains, e.g., 0.02 g of the DL-lactic acid, the amount of the lactotripeptide is preferably in a range of 60 to 100 µg in terms of VPP. If the fermented milk product contains a diluted fermented milk and contains, e.g., 0.005 g of the DL-lactic acid, the amount of the lactotripeptide is preferably 15 to 25 µg in terms of VPP. Although the fermented milk product of the present invention may contain L-lactic acid, which is a food additive for adjusting acidity, this L-lactic acid is to be distinguished from the DL-lactic acid generated during the fermentation.

The lactic acid bacteria in the fermented milk product of the present invention may be either sterilized after fermentation, or kept alive without sterilization.

The fermented milk product of the present invention may be yogurt, milk-containing acidified beverages, cheese, processed foods containing fermented sour milk, and healthy foods containing fermented sour milk. Thus, the fermented milk product of the present invention may contain, in addition to the fermented milk as the requisite component, various materials which are usually added for producing such a variety of products. The fermented milk product of the present invention may be in the form of solid such as powders, granules and tablets, or of fluid such as paste, gel and liquid.

The method for producing the fermented milk product of the present invention includes fermenting with the lactic acid bacteria a medium containing a food material selected from the group consisting of a peptide, a protein and mixtures thereof including Val-Pro-Pro and/or Ile-Pro-Pro as a part of its sequence.

The food material in the medium may be of any kind as long as it contains peptides and/or proteins including, as a part of their sequence, VPP and/or IPP. For example the food material may be animal milk, milk casein, corn, corn protein, wheat, wheat protein, soybean, soybean milk, de-fat soybean, soybean protein, or mixtures thereof. Particularly, it is preferable to employ a food material containing animal milk such as cow's milk, goat's milk, horse's milk, or skim milks of these. The content of the solid of non-fat milk in the animal milk is not particularly limited, but is usually 5 to 20 wt %.

There is no particular limitation on the amount of the lactic acid bacteria with which the medium is inoculated. The inoculation amount is usually about $10^5$ to $10^7$ cells of the lactic acid bacteria per 1 g of the aforementioned specific food material in the medium.

The fermentation may be performed at 25 to 50° C. and preferably 30 to 45° C., for 6 to 30 hours and preferably 10 to 24 hours, in the pH range of preferably 3.0 to 4.0, and more preferably 3.0 to 3.5.

The fermentation is preferably performed such that the amount of the lactotripeptide is not less than 60 µg in terms of VPP per ml of the resulting fermented milk. Specifically, when cow's milk containing 9 wt % solid of non-fat milk is employed as a medium, fermentation at 25 to 40° C. for 12 to 48 hours results in a fermented milk containing the lactotripeptide in an amount of not less than 70 µg in terms of VPP per ml. The content of the solid of non-fat milk in the medium is roughly proportional to the lactotripeptide to be produced. For example, if the food material contains 5 wt % solid of non-fat milk, the fermentation in accordance with the aforementioned conditions would result in production of the lactotripeptide in an amount of about 33.3 µg in terms of VPP per ml.

The fermented milk obtained by the aforementioned fermentation may be admixed with the product as it is. If necessary, the fermented milk may be subjected to dilution or purification before mixing. The fermented milk may be cooled and stored at 5° C., and then admixed with other components to prepare a product such as a chilled product. Alternatively, the fermented milk may be subjected to heat sterilization treatment, and, if necessary, powdered by spray drying to prepare a product for distributing at an ordinary temperature.

Since the fermented milk product of the present invention contains the fermented milk obtained by fermentation with the lactic acid bacteria, it can be used to prepare easily products having high content of the lactotripeptide with respect to the content of the lactic acid, in an agreeable form to take. The fermented milk product is expected to exhibit hypotensive effect and anti-stress effect of the lactotripeptide when taken by human being.

Since the lactic acid bacteria of the present invention can produce a large amount of the lactotripeptide by culturing them in the specific food material, the bacteria are useful in producing a variety of fermented milk products, functional foods, healthy foods, foods for specified health use, foods for specified use for elder people, and the materials thereof, having hypotensive effect and stress-relieving effect of the lactotripeptide.

EXAMPLES OF THE INVENTION

The present invention will be explained more in detail hereinbelow referring to the Examples, but the present invention is not limited thereto.

Among the *Lactobacillus helveticus* strains used in the Examples, CM4 strain (Taxonomy: Bacteria; Firmicutes; *Bacillus/Clostridium* group; Lactobacillales, Lactobacillaceae, *Lactobacillus, Lactobacillus helveticus*) was deposited on Aug. 15, 1997 at National Institute of Bioscience and Human-Technology Agency of Industrial Science and Technology, Ministry of International Trade and Industry, 1-3, Higashi 1 chome, Tsukuba-shi, Ibaraki-ken, 305 Japan and has been accorded accession number FERM BP-6060. ATCC15009, NCDO-099, JCM1006, ATCC10797, JCM1062, JCM1103, JCM1120, and JCM1004 are publicly available strains. Strains other than the above strains used in the Examples are selected from strain collection of the applicant.

Example 1

(Selection of Strains Giving Fermented Milk Having High ACE Inhibitory Activity)

36 strains of *Lactobacillus helveticus* isolated from various dairy products were screened. ACE inhibitory activity of milk fermented with each of the strains was measured by the following procedure. Each of the *Lactobacillus helveticus* strains was cultured in a 9 wt % solid of non-fat milk medium at 37° C. for 24 hours. The cultured medium was added to a fresh medium of the same type in such an amount that the new medium contains 3 wt % of the cultured medium. Fermentation was further performed at 37° C. for 24 hours. After finishing the fermentation, acidity of lactic acid (wt %), the amount of the peptide in the whey (mg/ml), the number of cells and ACE inhibitory activity (U/ml) were measured. The results are shown in Table 1.7 strains out of 36 strains had very weak fermentation ability. 15 strains produced fermented milk with the acidity of the lactic acid generated of not less than 1.6 wt %. Out of the 15 strains, 8 strains having ACE inhibitory activity of not less than 40 U/ml whey in its fermented milk were selected.

(Measurement of ACE Inhibitory Activity of Fermented Milk)

ACE inhibitory activity was measured in accordance with Cushman and Cheung's method (Cushman, D. W. and Cheung, H. S. Pharmacol., 201637 (1971)). That is, each of the fermented milk was centrifuged at 15,000 rpm for 5 minutes to obtain the supernatant (whey). The whey was suitably diluted for measurement. 80 µl of the diluted whey was put in a tube, admixed with 0.2 ml of 0.1M boric acid buffer (containing 0.3M NaCl, pH 7.3) containing 5 mM hippuryl histidine leucine (Hip-His-Leu, manufactured by SIGMA CHEMICALS CO.) as a substrate, and further admixed with 20 µl of enzyme solution (0.1 U/ml, manufactured by SIGMA CHEMICALS CO.). The resulting mixture was reacted at 37° C. for 30 minutes, and then admixed with 250 µl of 1N hydrochloric acid for terminating the reaction. Subsequently, the mixture was admixed with 1.7 ml of ethyl acetate, stirred for 20 seconds, and then centrifuged at 3,000 rpm for 10 minutes to recover 1.4 ml of ethyl acetate phase (upper phase). The upper phase was heated at 120° C. for 40 minutes to remove the solvent, admixed with 1 ml of distilled water, and stirred for about 20 seconds. The hippurylic acid extracted was measured for absorbance at 228 nm. The enzyme activity in unit was calculated by the following equation with the amount which gives 50% inhibition of the ACE activity being defined as one unit.

$$\text{Amount of the enzyme (unit)} = ((A-B)/(A-C)) \times 100 \times 1/50$$

A: Absorbance at 228 nm without sample
B: Absorbance at 228 nm with sample
C: Absorbance at 228 without enzyme nor sample (Quantitative Analysis of Amount of Peptides in the Fermented Milk)

Quantitative analysis of the peptides was performed in accordance with OPA method (Charch, F. C. et al. J. Dairy Sci. 66 1219(1883). As a standard substance for generating a calibration curve, casein digested with trypsin was employed.

TABLE 1

| Strains | Acidity (wt %) | Amount of Peptides (mg/ml) | Number of Cells (x10^8 cells/ml) | ACE Inhibitory activity(U/ml) |
| --- | --- | --- | --- | --- |
| strain 1 | — | — | — | — |
| strain 2 | — | — | — | — |
| strain 3 | — | — | — | — |
| strain 4 | — | — | — | — |
| strain 5 | — | — | — | — |
| strain 6 | — | — | — | — |
| strain 7 | — | — | — | — |
| strain 8 | 0.498 | 1.59 | 0.29 | 26.4 |
| strain 9 | 2.022 | 1.99 | 9.53 | 34.5 |
| strain 10 | 1.709 | 2.10 | 8.53 | 24.5 |
| strain 11 | 0.615 | 1.76 | 1.28 | 29.1 |
| strain 12 | 0.411 | 1.35 | 0.38 | 17.6 |
| strain 13 | 0.917 | 1.57 | 3.63 | 19.9 |
| strain 14 | 1.026 | 1.71 | 5.78 | 9.4 |
| strain 15 | 0.517 | 1.59 | 0.56 | 26.9 |
| strain 16 | 1.532 | 4.69 | 5.97 | 102.5 |
| strain 17 | 2.101 | 2.01 | 6.09 | 98.9 |
| strain 18 | 1.783 | 1.94 | 5.38 | 21.9 |
| strain 19 | 1.955 | 1.69 | 5.31 | 100.6 |
| strain 20 | 2.095 | 1.74 | 7.16 | 61.4 |
| strain 21 | 1.963 | 2.03 | 6.05 | 125.3 |
| strain 22 | 1.798 | 2.85 | 6.19 | 54.2 |
| strain 23 | 1.604 | 2.32 | 6.81 | 36.6 |
| strain 24 | 1.932 | 1.77 | 7.97 | 47.7 |
| strain 25 | 1.885 | 1.51 | 4.91 | 18.3 |
| strain 26 | 1.862 | 1.46 | 5.69 | 26.2 |
| strain 27 | 1.063 | 3.01 | 2.78 | 76.9 |
| strain 28 | 0.457 | 1.98 | 0.50 | 52.4 |
| strain 29 | 0.516 | 2.55 | 1.13 | 92.6 |
| JCM1006 | 1.872 | 2.35 | 6.97 | 48.5 |
| JCM1062 | 1.109 | 2.60 | 8.50 | 78.4 |
| JCM1103 | 1.244 | 1.36 | 3.69 | 31.0 |
| ATCC10797 | 1.359 | 2.11 | 8.56 | 13.8 |
| ATCC15009 | 1.454 | 1.81 | 5.16 | 16.6 |
| NCDO-099 | 1.769 | 2.76 | 6.59 | 25.5 |
| CM4 | 1.635 | 3.12 | 4.44 | 130.0 |

(Selection of Strains Having High Lactotripeptide Productivity)

Subsequently, the 8 strains which gave fermented milk having high ACE inhibitory activity as selected above were measured for VPP and IPP in their fermented milk.

1 ml of the fermented milk was centrifuged at 15,000 rpm for 10 minutes. The supernatant thereof, i.e. whey, was collected. 0.3 ml of the whey was subjected to Sep-Pak Cartridge (manufactured by WATERS INC.) adsorption, washed with distilled water, and then eluted with 5 ml of methanol. The eluate was dried under centrifugation and reduced pressure. The dried product was dissolved in 0.3 ml of a 0.05% aqueous solution of trifluoroacetic acid, and subjected to HPLC (high performance liquid chromatography) analysis under the following conditions. The results are shown in Table 2.

Apparatus Employed:
   Hitachi L4000UV detector (at 215 nm)
   L6200 intelligent pump
   L5030 column oven (35° C.)
Condition of Elution: Flow rate 0.5 ml/min.
Eluent: Aqueous solution containing 0.3M NaCl and 0.05% trifluoroacetic acid
Column: Asahipak GS320 (Φ3.9×600 mm)

Since the ACE inhibitory activity of IPP per unit weight is 1.7 times that of VPP, the amount of the lactotripeptides in terms of VPP was calculated from the measured amounts of IPP and VPP in accordance with the following equation. The results are shown in Table 2.

Converted amount of lactotripeptide (μg in terms of VPP per ml)=Amount of IPP (μg/ml)×1.7+Amount of VPP (μg/ml)

TABLE 2

| | Amount of Peptide (μg/ml whey) | | | |
| --- | --- | --- | --- | --- |
| Strains | VPP | IPP | Amount of lactotripeptide in terms of VPP | Acidity (wt %) |
| Strain 17 | 15.2 | 11.1 | 34.0 | 1.5 |
| Strain 19 | 11.2 | 7.3 | 23.7 | 1.4 |
| Strain 20 | 13.0 | 8.1 | 26.8 | 1.6 |
| Strain 21 | 16.6 | 11.4 | 36.0 | 1.6 |
| Strain 22 | 15.8 | 12.1 | 36.3 | 1.5 |
| Strain 24 | 12.6 | 8.7 | 27.4 | 1.6 |
| JCM1006 | 12.9 | 9.3 | 28.6 | 1.3 |
| CM4 | 38.5 | 23.5 | 78.5 | 1.9 |

CM4 fermented milk had the largest amount of the lactotripeptide in terms of VPP, that is, 78.5 μg/ml whey. Other seven strains gave the average amount of 34.2 μg/ml whey.

(Measurement of Extracellular Proteinase)

Extracellular proteinase activity was measured of 16 strains which gave relatively good results in fermentability shown in Table 1. Measurement was performed in accordance with the method of Yamamoto et al. (Yamamoto, N. et al. J. Biochem. (1993) 114, 740) based on the method of Twining et al. (Twining, S. Anal. Biochem 143, 3410 (1984)). That is, each strain was cultured in 9 wt % skim milk medium while pH thereof was maintained at 6.0. Sample was taken in the middle of logarithmic growth phase, and admixed with sodium citrate so that the final concentration was 1 wt %, for clarifying the milk medium. The mixture was centrifuged at 5,000 rpm for 10 minutes to collect cells. The cells were washed with 50 mM β-glycerophosphoric acid, and suspended in 50 mM Tris-HCl buffer (pH 7.8) to adjust turbidity ($OD_{590}$, i.e. measured by absorbance at 590 nm) to 1.30 μl of the suspension was admixed with 20 μl of 0.4% fluorescein-casein (manufactured by SIGMA CHEMICALS CO.), and incubated at 42° C. for 1 hour. The mixture was further admixed with 120 μl of 5% trichloroacetic acid, allowed to stand for 20 minutes, and centrifuged at 15,000 rpm for 10 minutes. 60 μl of the supernatant was added to 3 ml of 500 mM tris-HCl buffer (pH 8.3), and the fluorescent intensity thereof was measured by detecting the fluorescence of 525 nm produced at an excitation wavelength of 490 nm. Extracellular proteinase activity in unit was calculated with the amount of the enzyme which exhibits 1% fluorescent intensity under the above conditions being defined as one unit. The results are shown in Table 3.

TABLE 3

| Strains | $U/OD_{590}$ |
| --- | --- |
| strain 17 | 136.7 |
| strain 18 | 102.8 |
| strain 19 | 103.2 |
| strain 20 | 89.9 |
| strain 21 | 80.1 |
| strain 22 | 243.3 |
| strain 23 | 116.6 |

TABLE 3-continued

| Strains | U/OD$_{590}$ |
|---|---|
| strain 24 | 116.6 |
| strain 25 | 192.6 |
| strain 26 | 108.4 |
| JCM1006 | 185.7 |
| JCM1062 | 96.5 |
| JCM1103 | 176.3 |
| ATCC15009 | 168.1 |
| ATCC10797 | 106.5 |
| NCDO-099 | 229.7 |
| CM4 | 452.6 |

The activity of *Lactobacillus helveticus* CM4 was the highest, that is, 450 U/OD$_{590}$. Average activity for other 16 strains was 141 U/OD$_{590}$, which is about one third of that of CM4 strain.

Example 2

From 11 strains out of 36 *Lactobacillus helveticus* strains selected in Example 1, chromosomal DNA was extracted in accordance with the method of Leenhouts et al. (Leenhouts, K. (1990) Appl. Environ. Microbiol. 56:2726), digested with several restriction enzymes, and subjected to 0.8% agarose gel electrophoresis to analyze the electrophoresis pattern.

As a result, a characteristic DNA fragment was observed among DNA fragments of chromosome of CM4 strain digested with EcoRI and PstI (shown by arrow 1 in FIG. 1). Such a fragment was not observed in the fragments of chromosomes from other strains than CM4, and shorter fragments than the characteristic fragment of CM4 were observed in most of other strains (shown by arrow 2 in FIG. 1). The molecular weight of the characteristic fragment was measured by comparative electrophoresis of the Hind III digestion products of λ phage DNA as size markers (230.1 kb, 9.4 kb, 6.6 kb, 4.4 kb, 2.3 kb and 2.0 kb, in the order of increasing mobility), and was found to be about 16 kb. Thus, it was confirmed that CM4 strain has a chromosomal DNA which gives the DNA fragment having molecular weight of about 16 kb, by digestion with EcoRI and PstI. It was also confirmed that other strains than CM4 have chromosomal DNA which give a common DNA fragment having molecular weight of about 13 kb.

Example 3

A fermented milk was produced with *Lactobacillus helveticus* CM4 strain selected in Example 1. CM4 strain was cultured in 100 g of 9 wt % skim milk at 37° C. for 12 hours. Subsequently, 3 kg of fresh medium was inoculated with the cultured skim milk, and cultured at 37° C. for 12 hours. After finishing the fermentation, all of the fermented milk (number of cells of CM4 strain; 6.3×10$^8$ cells/ml) was used as a starter for fermentation of 100 kg of 9 wt % skim milk at 32° C. for 20 hours. After finishing the fermentation, 74.8 μg/ml of the lactotripeptide was contained in the fermented milk. The content of the lactic acid was 1.9 wt %.

43 kg of the obtained fermented milk was admixed with 4 kg of granulated sugar, 3 kg of water and 0.15 kg of high methoxypectin, and homogenized to obtain 50 kg of yogurt drink. The yogurt beverage had a preferable mild taste, pH of 3.6 and 4.6×10$^8$ cells/g of live CM4 cells.

Example 4

26.5 kg of the fermented milk obtained in Example 3 was admixed with 45.0 kg of granulated sugar, 4.7 kg of high maltose syrup and 13.8 kg of water. 10 kg of 3 wt % high methoxypectin solution was added to the mixture under stirring. The resulting mixture was homogenized using a laboratory homogenizer (manufactured by ATV GAULIN, INC., Model 15M-8BA) under a treatment pressure of 150 kg/cm$^2$ and at a treatment flow rate of 2500 ml/min. The homogenized liquid was admixed with a vanilla flavor and sterilized by heating up to 85° C. The fermented milk thus sterilized was charged in a 200 ml glass bottle while hot. The content of the lactotripeptide in the sterilized fermented milk product was measured. It was found out that the content of the lactotripeptide corresponded to that in the fermented milk before sterilization. It was also found out that the content of the lactic acid was 0.5 wt %.

What is claimed is:

1. A method for producing a fermented milk product containing *Lactobacillus helveticus* and a tripeptide selected from the group consisting of Val-Pro-Pro, Ile-Pro-Pro and mixtures thereof, said method comprising fermenting a medium containing milk comprising a peptide, a protein or mixtures thereof including sequence Val-Pro-Pro and Ile-Pro-Pro, with *Lactobacillus helveticus* CM4, FERM BP-6060.

2. The method of claim 1, wherein said milk is selected from the group consisting of animal milk, skim milk, milk casein, soybean milk, and mixtures thereof.

3. The method of claim 1, wherein the fermenting is performed at 25 to 50° C. for 6 to 60 hours.

* * * * *

UNITED STATES PATENT AND TRADEMARK OFFICE
CERTIFICATE OF CORRECTION

| | | |
|---|---|---|
| PATENT NO. | : 7,282,354 B2 | Page 1 of 1 |
| APPLICATION NO. | : 10/310628 | |
| DATED | : October 16, 2007 | |
| INVENTOR(S) | : Naoyuki Yamamoto et al. | |

It is certified that error appears in the above-identified patent and that said Letters Patent is hereby corrected as shown below:

On The Title Page Item (30)

Please Insert --PCT/JP98/00481 Feb. 5, 1998--.

For Foreign Application Priority Data, please insert -- JP 9-277949 Sept. 26, 1997--.

Signed and Sealed this

Eighteenth Day of December, 2007

JON W. DUDAS
*Director of the United States Patent and Trademark Office*